(12) United States Patent
Jureczek

(10) Patent No.: US 7,553,499 B2
(45) Date of Patent: Jun. 30, 2009

(54) SUSTAINED RELEASE TABLET CONTAINING INDAPAMIDE

(75) Inventor: Katarzyna Jureczek, Kraków (PL)

(73) Assignee: Pliva Krakow, Zaklady Farmaceutyczne S.A., Krakow (PL)

( * ) Notice: Subject to any disclaimer, the term of this patent is extended or adjusted under 35 U.S.C. 154(b) by 670 days.

(21) Appl. No.: 10/518,386

(22) PCT Filed: Jul. 24, 2002

(86) PCT No.: PCT/PL02/00056

§ 371 (c)(1),
(2), (4) Date: May 3, 2005

(87) PCT Pub. No.: WO2004/002475

PCT Pub. Date: Jan. 8, 2004

(65) Prior Publication Data

US 2005/0202086 A1    Sep. 15, 2005

(30) Foreign Application Priority Data

Jul. 1, 2002    (PL) .................................... 354823

(51) Int. Cl.
*A61K 9/26* (2006.01)
*A61K 9/22* (2006.01)

(52) U.S. Cl. .................. 424/470; 424/464; 424/468

(58) Field of Classification Search .................. 424/472, 424/464, 474, 475, 468, 470
See application file for complete search history.

(56) References Cited

U.S. PATENT DOCUMENTS 5,334,392 A    8/1994  Cuine et al.
6,077,534 A *  6/2000  Tobin et al. .................. 424/462
6,294,200 B1 * 9/2001  Conte et al. .................. 424/472

FOREIGN PATENT DOCUMENTS

| DE | 3602304 | 8/1986 |
|---|---|---|
| EP | 0519820 | 12/1992 |
| EP | 1057479 | 12/2000 |
| GB | 2123293 | 2/1984 |
| GB | 2173399 | 10/1986 |

OTHER PUBLICATIONS

Damien et al, Galenic Development and Pharmacokinetic Profile of indapamide Sustained Release 1.5mg, 1999, Clin Pharmaco, 37, Suppl 1 (XP009004369).*
G. Damien et al., Clinical Pharmacokinetics, vol. 37, Suppl. 1, pp. 12-19, 1999.

* cited by examiner

*Primary Examiner*—Michael G Hartley
*Assistant Examiner*—Micah-Paul Young
(74) *Attorney, Agent, or Firm*—Foley & Lardner, LLP

(57) ABSTRACT

The present invention relates to a sustained release tablet containing indapamide and the process of manufacturing sustained release tablet containing indapamide. The tablet contains indapamide in the amount of 1.5 to 2.5% of the total mass of the tablet, lactose monohydrate in the amount of 30 to 80% of the total mass of the tablet, copovidone in the amount of 2 to 10% of the total mass of the tablet, hypromellose in the amount of 20 to 65% of the total mass of the tablet and lubricants in the amount of 0.1 to 5% of the total mass of the tablet. The process of manufacturing the sustained release tablet consists in mixing of indapamide with lactose monohydrate and copovidone and then, the mixture is moistened by purified water and the granulation process of it is performed. Next the granulate is dried, cooled, mixed with hypromellose and lubricants and compressed in tableting machine.

6 Claims, No Drawings

SUSTAINED RELEASE TABLET CONTAINING INDAPAMIDE

BACKGROUND OF THE INVENTION

1. Field of the Invention

The present invention relates to a sustained release tablet containing indapamide and the process of manufacturing sustained release tablet containing indapamide, known medicinal product of diuretic activity administered in the therapy of primary hypertension.

2. Discussion of Background Information

From a specification of the patent No: EP 519820 it is known a sustained release matrix tablet of indapamide and a process of its manufacturing. Sustained release is controlled by the use of methylhydroxypropylcellulose and polyvidone, the percentages of which are from 30 to 50% and from 2 to 10%, respectively, of the total mass of the tablet. The percentages of the cellulose and polyvidone compounds permit the sustained release of indapamide in a manner that is linear for a period of at least eight hours and the release of 50% of the total quantity of indapamide within a period of from 5 to 14 hours. Additionally, the percentages of cellulose and polyvidone compounds permit the sustained release of indapamide to give blood levels in humans of from 20 to 80 ng/ml at most after administration of the tablet by the oral route. A process for the preparation of an indapamide matrix tablet known from the patent No. EP 519820 is based on that there are used both a moist granulation technique and a direct compression technique, comprising the steps as follows. First, indapamide, polyvidone and lactose are mixed, then moistened with an aqueous-alcoholic solution to yield a moist mass which is then granulated, dried and then graded so as to obtain a granulate whose physical characteristics allow good filling of the moulds of a rapid compression machine. The obtained granulate is mixed with methylhydoxypropylcellulose and lubricated with magnesium stearate and colloidal silica. The final step is compression of the lubricated mixture in a rotary compression machine, so as to obtain tablets having a hardness of approximately from 60 to 75 N.

SUMMARY OF THE INVENTION

According to the invention, the tablet for the sustained release containing indapamide contains indapamide in the amount 1.5 to 2.5% of the total mass of the tablet, lactose monohydrate in the amount of 30 to 80% of the total mass of the tablet, copovidone in the amount of 2 to 10% of the total mass of the tablet, hypromellose in the amount of 20 to 65% of the total mass of the tablet and lubricants in the amount of 0.1 to 5% of the total mass of the tablet. The aim of the use of copovidone is to bind all tablet components. Hypromellose modifies the release of the active ingredient, which is indapamide.

Magnesium stearate or/and anhydrous colloidal silica are used as the lubricants.

Hypromellose viscosity is between 1,000 to 20,000 cP.

According to the invention the process of manufacturing the sustained release tablet containing indapamide consists in mixing indapamide with lactose monohydrate and copovidone. Then, the mixture is moistened by purified water and granulated. The obtained granulate is then dried, cooled, mixed with hypromellose and lubricants and compressed in tableting machine.

DETAILED DESCRIPTION OF THE INVENTION

The aim of the invention was to simplify the process of manufacturing the sustained release tablet containing indapamide. Additionally, it allowed replacing alcohol with water with improved safety of the manufacturing process and reduced its impact on the environment.

Examples of the invention are presented below:

EXAMPLE I 25 g of indapamide and 225 g of lactose monohydrate is mixed manually, the mixture is poured into a granulate-mixer together with 487 g of lactose monohydrate and is mixed within 1 minute with the main agitator speed 200 rpm.

Then 487 g of lactose monohydrate and 60 g of copovidone is added and all components are mixed for 1 minute with the main agitator speed 200 rpm and then with the main agitator speed 200 rpm and the side agitator speed 400 rpm.

To the prepared mixture 100 g of purified water is added within 1 minute with the main agitator speed 200 rpm and the side agitator speed 400 rpm. Then, the granulation process is performed within 4 minutes with the main agitator speed 400 rpm and side agitator speed 800 rpm.

Wet granulate is rubbed through the screen of 2.5 mm mesh and dried in the fluidal drier in the temperature 40° C. to humidity content below 1% The dried granulate is sieved through the screen 1.2 mm mesh.

In the following step mixing of the granulate with the rest of components is performed in the rotary mixer with speed 20 rpm.

Into rotary mixer 642 g of granulate with 350 g of hypromellose is poured and mixed within 10 minutes, after which 642 g of granulate is added and is mixed within 10 minutes. Then, 350 g of hypromellose is added with 6 g of colloidal silica and is mixed within 15 minutes, after which 10 g of magnesium stearate is added and mixed within 5 minutes.

Finally tableting process of the prepared mixture is performed.

EXAMPLE II 25 g of indapamide and 225 g of lactose monohydrate is mixed manually and next the mixture is poured into granulate-mixer together with 507 g of lactose monohydrate and is mixed within 1 minute with the main agitator speed 200 rpm.

Then 507 g of lactose monohydrate and 60 g of copovidone is added and all components are mixed within 1 minute with the main agitator speed 200 rpm and 1 minute with the main agitator speed 200 rpm and the side agitator speed 400 rpm.

To the mixture obtained in such way 100 g of purified water is dosed within 1 minute with the main agitator speed 200 rpm and the side agitator speed 400 rpm.

Next the granulation process is performed within 4 minutes with the main agitator speed 400 rpm and the side agitator speed 800 rpm.

Wet granulate is rubbed through a screen 2.5 mm mesh and is dried in the fluidal drier in the temperature 40° C. to humidity content below 1%. The dried granulate is sieved through the screen 1.2 mm mesh.

In the following step the mixing granulate with the rest of components is performed in the rotary mixer with the speed 20 rpm. Into rotary mixer 662 g of granulate with 330 g of hypromellose is poured and mixed within 10 minutes. Then, 662 g of the granulate is added and mixed within 10 minutes, after which 330 g of hypromellose together with 6 g of colloidal silica is added and mixed within 15 minutes, and next 10 g of magnesium stearate is added and mixed within 5 minutes.

Finally tableting process of the prepared mixture is performed.

The invention may be used in the industrial process of manufacturing sustained release tablets containing indapamide.

The invention claimed is:

1. Sustained release tablet comprising 1.5 to 2.5% of total mass of the tablet of indapamide, 30 to 80% of total mass of the tablet of lactose monohydrate, 2 to 10% of total mass of the tablet of copovidone, 20 to 65% of total mass of the tablet of hypromellose, and 0.1 to 5% of total mass of the tablet of lubricant, wherein the tablet is prepared by a method comprising mixing indapamide with lactose monohydrate and copovidone and then moisturizing the mixture with purified water and performing granulation after which the granulate is dried, cooled, mixed with hypromellose and lubricant and compressed in a tableting machine.

2. The tablet according to claim 1, wherein said lubricant comprises at least one of magnesium stearate and anhydrous colloidal silica.

3. The tablet according to claim 1, wherein the hypromellose has a viscosity from 1,000 to 20,000 cP.

4. Process of manufacturing sustained release tablet containing indapamide, comprising mixing indapamide with lactose monohydrate and copovidone and then moisturizing the mixture with purified water and performing granulation after which the granulate is dried, cooled, mixed with hypromellose and lubricant and compressed in a tableting machine, wherein the tablet comprises 1.5 to 2.5% of total mass of the tablet of indapamide, 30 to 80% of total mass of the tablet of lactose monohydrate, 2 to 10% of total mass of the tablet of copovidone, 20 to 65% of total mass of the tablet of hypromellose, and 0.1 to 5% of total mass of the tablet of lubricant.

5. The process according to claim 4, wherein said lubricant comprises at least one of magnesium stearate and anhydrous colloidal silica.

6. The process according to claim 4, wherein the hypromellose has a viscosity from 1,000 to 20,000 cP.

* * * * *

UNITED STATES PATENT AND TRADEMARK OFFICE
CERTIFICATE OF CORRECTION

| | | |
|---|---|---|
| PATENT NO. | : 7,553,499 B2 | Page 1 of 1 |
| APPLICATION NO. | : 10/518386 | |
| DATED | : June 30, 2009 | |
| INVENTOR(S) | : Jureczek | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 670 days Delete the phrase "by 670 days" and insert -- by 1,038 days --

Signed and Sealed this

Twenty-third Day of March, 2010

David J. Kappos
*Director of the United States Patent and Trademark Office*